(12) United States Patent
Nicolas et al.

(10) Patent No.: US 11,931,551 B2
(45) Date of Patent: Mar. 19, 2024

(54) MEDICAL INJECTION SYSTEM

(71) Applicant: Becton Dickinson France, Le Pont de Claix (FR)

(72) Inventors: Maxime Nicolas, Grenoble (FR); Julien Gagliano, Grenoble (FR)

(73) Assignee: Becton Dickinson France, Le Pont de Claix (FR)

( * ) Notice: Subject to any disclaimer, the term of this patent is extended or adjusted under 35 U.S.C. 154(b) by 795 days.

(21) Appl. No.: 17/045,817

(22) PCT Filed: Apr. 8, 2019

(86) PCT No.: PCT/EP2019/058786
§ 371 (c)(1),
(2) Date: Oct. 7, 2020

(87) PCT Pub. No.: WO2019/197325
PCT Pub. Date: Oct. 17, 2019

(65) Prior Publication Data
US 2021/0138154 A1    May 13, 2021

(30) Foreign Application Priority Data
Apr. 9, 2018 (EP) .................................. 18305414

(51) Int. Cl.
*A61M 5/20* (2006.01)
*A61M 5/31* (2006.01)

(52) U.S. Cl.
CPC ........ *A61M 5/2046* (2013.01); *A61M 5/3137* (2013.01); *A61M 2205/75* (2013.01)

(58) Field of Classification Search
CPC ................ A61M 5/155; A61M 5/2466; A61M 2005/14513; A61M 5/2053; A61M 5/283; A61M 2005/3132; A61M 5/2046; A61M 5/3137; A61M 2005/14204; A61M 2205/8218; A61M 5/8231
See application file for complete search history.

(56) References Cited

U.S. PATENT DOCUMENTS

| 3,853,125 | A | 12/1974 | Clark et al. |
| 6,096,002 | A | 8/2000 | Landau |
| 7,559,917 | B2 * | 7/2009 | Alexandre ............. A61M 5/30 604/143 |
| 10,800,597 | B2 * | 10/2020 | Kolonia ............ A61M 5/3134 |
| 2006/0089601 | A1 | 4/2006 | Dionigi |

(Continued)

*Primary Examiner* — Tasnim Mehjabin Ahmed
*Assistant Examiner* — Kayla M. Turkowski
(74) *Attorney, Agent, or Firm* — The Webb Law Firm

(57) ABSTRACT

A medical injection system adapted for a single-handed injection, the medical injection device comprising a gas compartment configured to contain a gas, the gas compartment comprising a piston, a reservoir intended to contain a drug composition, the reservoir having a proximal portion and a distal portion provided with a fluid exit configured to receive an injection needle, wherein the piston can move proximally between a distal position defining a first volume of the gas compartment to a proximal position defining a second volume of the gas compartment smaller than the first volume, and wherein the gas compartment is in gas communication with the reservoir in order to force the drug composition through the fluid exit, when the piston is moved proximally.

17 Claims, 2 Drawing Sheets

(56) References Cited

U.S. PATENT DOCUMENTS

| | | | | |
|---|---|---|---|---|
| 2008/0257915 A1* | 10/2008 | Wold | ............... | A61M 11/007 |
| | | | | 222/389 |
| 2009/0018512 A1* | 1/2009 | Charles | ............ | A61F 9/0017 |
| | | | | 604/117 |
| 2011/0046604 A1* | 2/2011 | Felsovalyi | ........... | A61M 5/19 |
| | | | | 604/218 |
| 2014/0135707 A1 | 5/2014 | Suzuki et al. | | |

* cited by examiner

MEDICAL INJECTION SYSTEM

CROSS-REFERENCE TO RELATED APPLICATIONS

This application is the United States national phase of International Application No. PCT/EP2019/058786 filed Apr. 8, 2019, and claims priority to European Patent Application No. 18305414.7 filed Apr. 9, 2018, the disclosures of which are hereby incorporated by reference in their entirety.

FIELD OF THE INVENTION

The present invention relates to a medical injection system for a single-handed injection.

BACKGROUND OF THE INVENTION

Medical syringes are widely used to deliver parenteral drugs to the human or animal body, for example by intravenous, intramuscular or subcutaneous injection. A typical medical syringe comprises an injection needle to perform skin pricking and drug transfer toward the patient's body, a syringe barrel containing a drug, a stopper travelling through the syringe barrel to force the drug through the injection needle and a plunger rod connected to the stopper in order to transmit a force to the stopper.

When an injection is performed with such a prior-art medical syringe, the force applied to the plunger rod by the medical caregiver's thumb directly determines the injection pressure and such an injection operation requires a precise control of this thrust to avoid any jerking movements during the injection. At the same time, the needle depth inserted into the patient's body must also be controlled by firmly holding the syringe barrel with two other fingers. Consequently, performing an efficient and painless injection with a prior-art medical syringe can be difficult and requires experience.

Furthermore, the syringe barrel, the injection needle and the plunger rod are long elements that require a bulky packaging, which could waste storage space in pharmacies. Finally, some people are scared by the typical appearance of a medical syringe and could feel fear and stress at the sight of one of them.

Consequently, there is a need for a medical injection system allowing a safe and comfortable injection both for the medical caregiver and the patient. In addition, there is also a need for a medical injection system adapted to save storage space and to reduce the patient's stress.

SUMMARY OF THE INVENTION

This objective is accomplished by a medical injection system adapted for a single-handed injection, the medical injection device comprising:

a gas compartment configured to contain a gas, the gas compartment comprising a piston, a reservoir intended to contain a drug composition, the reservoir having a fluid exit configured to receive an injection needle, wherein the piston is configured to move proximally between a distal position defining a first volume of the gas compartment to a proximal position defining a second volume of the gas compartment smaller than the first volume, and wherein the gas compartment is configured to be in gas communication with said reservoir in order to force the drug composition through the fluid exit, when the piston is moved proximally.

Consequently, the proximal movement of the piston operates a gas transfer from the gas compartment to the reservoir in order to perform the injection of a drug to a patient, when a drug is filled in the reservoir. The injection is thus performed by the pneumatic action resulting from the gas transfer.

The movement of the piston may be performed in the proximal direction that is in the direction opposite to the injection direction. This reduces or eliminates any jerking movements and ensures a smooth and comfortable injection operation. Finally, the piston avoids any stopper in a slidable engagement within the reservoir, which prevents any problem of compatibility between a drug composition and a lubricant usually required by such a stopper.

Preferably, the gas compartment further comprises a housing, and the piston is configured to move relative to the housing.

Again preferably, the reservoir is attached to the gas compartment, for example to the housing. This allows to design a smaller and more convenient medical injection system that may fit easily in the hand of a medical caregiver.

Preferably, at least part of the piston is located distally from the reservoir, at least in the distal position. This allows to produce a more compact and more convenient medical injection system.

Preferably the piston comprises at least one finger flange configured to be pushed proximally by a user. The finger flange is preferably located distally from the reservoir.

In a preferable embodiment, the reservoir is located within the gas compartment, which allows a compact and integrated design which does not appear as a typical medical syringe.

Preferably, the gas compartment is located coaxially and around the reservoir. In other words, the reservoir is included and surrounded by the gas compartment, which allows a very compact design allowing the use of compact packaging in order to save storage space. In addition, such a compact medical injection system may be easier to handle for a medical caregiver. For example, a longitudinal symmetry axis of the reservoir is co-linear with a longitudinal symmetry axis of the gas compartment.

For example, the reservoir has a proximal end and a distal end and the fluid exit is provided on the distal end.

Preferably, the reservoir comprises a proximal portion defining a handling surface which is adapted to accommodate a thumb of a medical caregiver, and the piston is provided with at least one finger flange adapted to accommodate at least another finger of the medical caregiver. This allows easy control of the inserted needle depth during the pricking operation of the patient's skin, by controlling the thrust applied by the thumb. In addition, the injection operation may be realized by squeezing the finger flange in the proximal direction, thus in the direction opposite from the injection direction.

A user-friendly injection operation is thus ensured and any variation of the inserted needle depth is limited or prevented during the injection operation, thus allowing a safe and comfortable injection. For example, two or three finger-flanges may be provided or a single finger-flange may allow to accommodate two or three different fingers.

Preferably, a sealing member is provided between the piston and the housing, which may improve the gas-tightness of the gas compartment. The sealing member may be an O-ring.

In an embodiment in which the gas compartment is located coaxially and around the reservoir, the proximal movement of the piston may require a sliding movement on a distal portion of the reservoir such as a neck, or on an injection needle, when an injection needle is provided. In this case, another sealing member may be provided between the piston and the reservoir or the injection needle, in order to improve the gas-tightness of the air compartment.

Preferably, the gas compartment is in gas communication with the proximal portion of the reservoir, which allows an optimal transfer of the gas into the reservoir. Again preferably, the gas compartment is only in gas communication with the proximal portion of the reservoir.

For example, a gas communication interface is provided between the gas compartment and the reservoir. The gas communication interface preferably comprises at least one orifice allowing the gas transfer. This gas communication interface may be the only gas communication interface of the gas compartment and/or may comprise at least two orifices or more.

Preferably, the gas communication interface is configured to prevent the transmission of any liquid from the reservoir to the gas compartment. This avoids wasting valuable drug composition and ensures that a consistent volume of drug composition is injected into the patient.

Preferably, the gas communication interface and for example the at least one orifice comprises a valve member, a filter member or a breakable membrane in order to prevent the transmission of any liquid from the reservoir to the piston.

Preferably, the proximal portion of the reservoir and the proximal end of the housing comprise a filling hole giving access to the inside of the reservoir.

In a more preferable embodiment of the present invention, the distal portion of the reservoir is provided with a stacked injection needle, which simplifies the injection by providing to a medical caregiver a medical injection system ready to be used.

Another aspect of the present invention relates to a medical injection system adapted for a single-handed injection, the medical injection device comprising:
  a cylindrical reservoir intended to contain a drug composition, the cylindrical reservoir having a proximal portion and a distal portion which is provided with a fluid exit configured to receive an injection needle,
  a cylindrical gas compartment intended to contain a gas and in gas communication with the reservoir,
  wherein the gas compartment has a distal end provided with a piston configured to move from a distal position to a proximal position in which the gas is transferred from the gas compartment to the reservoir.

For example, the piston defines a first volume of the gas compartment in the distal position and a second volume of the gas compartment in the proximal position.

Preferably, the reservoir and the gas compartment are fixed on to the other and may have each a longitudinal axis parallel to one another, that is the gas compartment and the reservoir are adjacent and aligned with the other.

A last aspect of the present invention is a method to use a medical injection system according to the first aspect or the second aspect, wherein a medical caregiver grasps the medical injection system by placing a thumb on the handling surface and another finger on the finger flange.

Preferably, a pricking operation is performed by positioning the injection needle of the medical injection system onto a patient's skin and applying a thrust on the handling surface with the thumb.

Again preferably, an injection operation is performed by squeezing or pinching another finger toward the thumb, in order to move the piston of the gas compartment from the distal position toward the proximal position.

BRIEF DESCRIPTION OF THE DRAWINGS

Further advantages and preferred embodiments of the present invention will become apparent from the following detailed description and drawings, in which.

DETAILED DESCRIPTION

The present medical injection system is intended for administration of parenteral drugs by a medical caregiver preferably using a single hand. In addition, the present medical injection system is preferably prefilled, that is to say that the medical injection system is produced and then filled with a drug composition before shipping to pharmacies. Consequently, the drug composition is available for the medical caregiver in the medical injection system and ready for injection, which minimises the operations performed by the medical caregiver before an injection operation and thus reduces the risk of accident or misuse.

As such, in this application, the distal direction must be understood as the direction of injection with reference to the medical injection system, and the proximal direction is the opposite direction, i.e. the direction toward the hand of the medical caregiver. In addition, a drug composition must be understood as all kind of injectable drug composition adapted for therapeutics, aesthetics, preventive or diagnosis applications.

Figure 1:
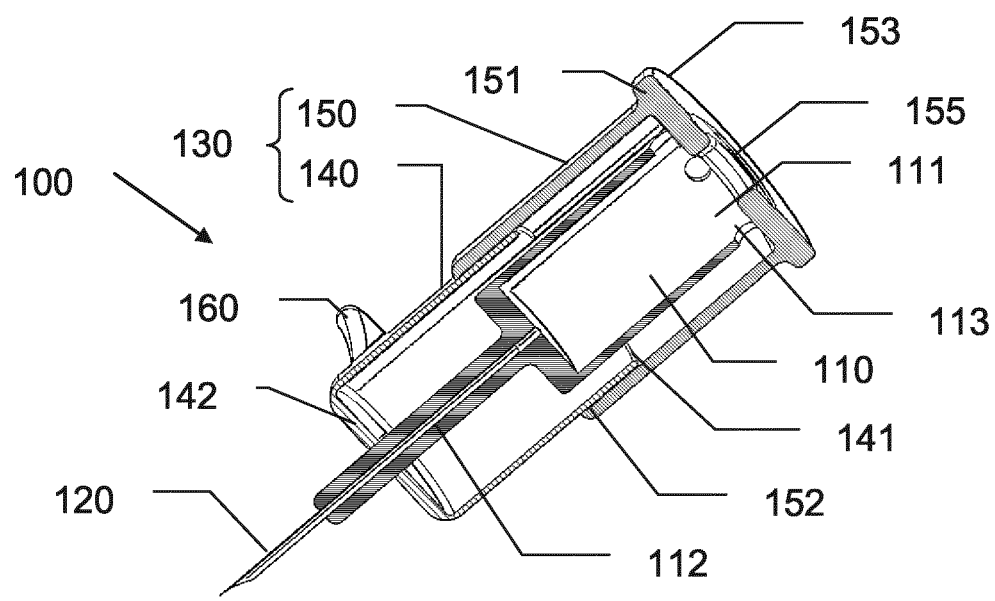
FIG. 1 is a cross-section view of a medical injection system according to the present invention.

Now regarding FIG. 1, a medical injection system 100 according to the present invention comprises a reservoir 110 provided with a back or proximal portion 111 and a neck or distal portion 112. The reservoir is preferably of cylindrical shape. An injection needle 120 is attached or stacked to the distal portion 112 of the reservoir 110. The reservoir is intended to contain a drug composition to be injected to a patient through the injection needle 120. The reservoir may comprise any material adapted to a medical application, such as glass or plastic, such as polypropylene or polycarbonate.

The reservoir 110 is preferably inserted into a gas compartment 130. The gas compartment defines a cavity intended to contain a gas. In this example, the gas compartment 130 comprising a piston 140 and a housing 150. The piston 140 is configured to move relative to the housing 150 in order to reduce the volume of the gas compartment 130. In this example, the piston 140 is configured to run on the distal portion 112 of the reservoir 110 and to slide or run into the housing 150 of the gas compartment in order to apply pressure on a gas contained in the gas compartment 130. The gas compartment 130 may comprise glass, metal, such as aluminium, or rigid plastic such as polycarbonate or polypropylene.

The housing 150 surrounds the reservoir 110 with the exception of the distal portion 112. The housing 150 includes a proximal end 151 overlapping the proximal portion 111 of the reservoir 110 and an opened distal end 152 that accommodates the proximal end 141 of the piston 140. The proximal end 151 comprises a radial rim that may allow to place the medical injection system in a standard packaging such as a nest.

The gas compartment 130 is thus located around and in parallel with the reservoir 110: a longitudinal axis of the reservoir 110 is co-linear with longitudinal axes of the piston 140 and the housing 150 of the gas compartment 130. In the embodiment of FIG. 1, these longitudinal axes are symmetry axes of the reservoir 110 and the gas compartment 130. The gas compartment 130 is thus coaxial or concentric with the reservoir 110 and surrounds the reservoir 110.

Gas-tight engagements between the reservoir 110, the piston 140 and the housing 150 allow a movement of the piston 140 to optimally apply a pressure on a gas contained in the gas compartment 130. This gas may be air or a non-reactive gas such as nitrogen or argon. For example, the piston 140 can comprise a first O-ring (not represented) on its proximal end 141 in order to ensure a gastight engagement with an internal surface of the housing 150. A second O-ring can be provided on the distal end 142 of the piston 140 in order to ensure a gastight engagement with the distal portion 112 of the reservoir 110 and/or with the injection needle 120.

Figure 2:
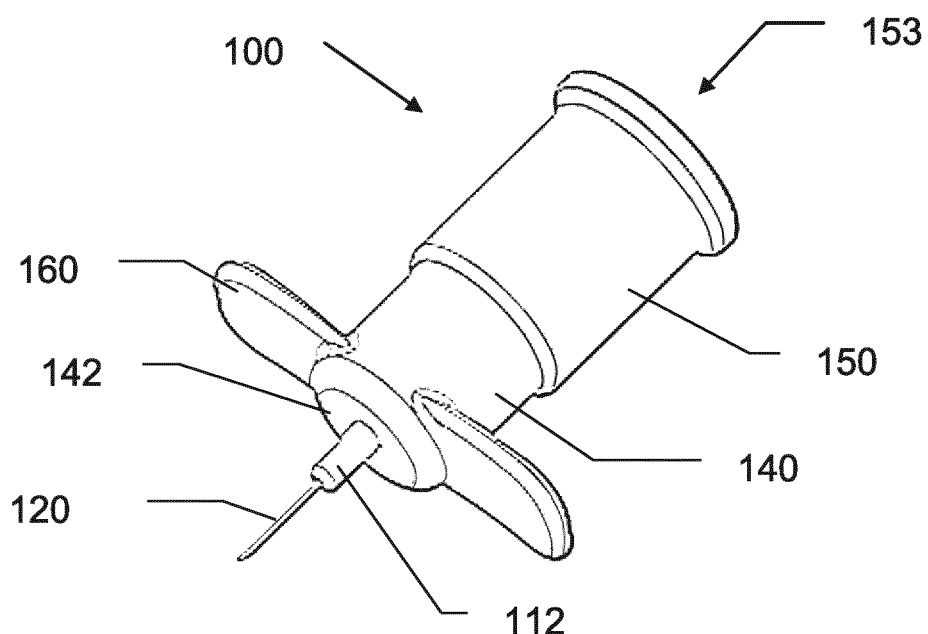
FIG. 2 is a three-dimensional external view of the medical injection system according to FIG. 1.
Figure 3:
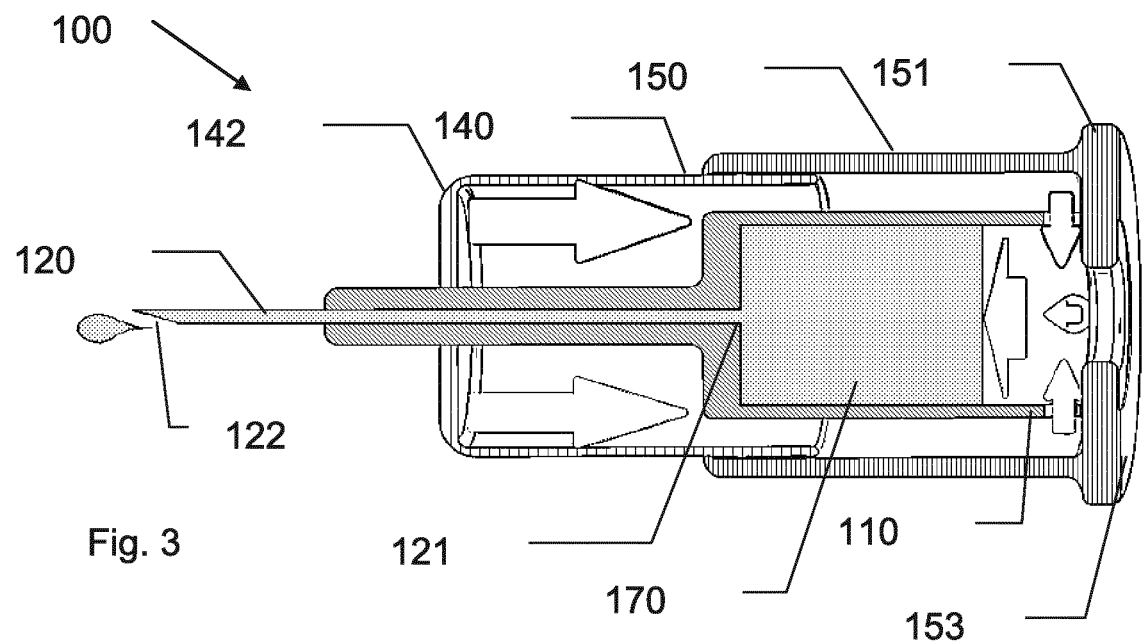
FIG. 3 is a cross-section view of the medical injection system according to FIG. 1 when an injection is performed.

Consequently, the piston 140 can adopt a distal position in view of the housing 150, represented in FIGS. 1-3, in which the inside volume of the gas compartment 130 (or first volume) is maximum and in which no pressure is applied on the gas contained in the gas compartment 130. Further, the piston 140 can also adopt a proximal position shown in FIG. 4 in which it may be completely slid into the housing 150 and in which the inside volume of the gas compartment 130 (or second volume) is minimal. A pressure is thus applied in the proximal position of the gas compartment 130 on the gas contained in the gas compartment 130 and such a gas may be forced or transferred out of the gas compartment 130.

In addition, the interior of the gas compartment 130 may be in gas communication with the proximal portion 111 of the reservoir 110. Indeed, the proximal portion 111 of the reservoir 110 comprises a gas communication interface provided with at least one and preferably several orifices 113, that allow the gas contained in the gas compartment 130 to be transmitted to the reservoir 110. Consequently, the gas can flow from the gas compartment 130 into the reservoir 110 upon movement of the piston 140 from the distal position to the proximal position and no other gas communication interface may be provided to the gas compartment 130.

In particular, the gas communication interface may be configured to prevent the transmission of any liquid from the reservoir 110 to the gas compartment 130. For example, the orifices 113 may be of a tiny diameter, such as few millimetres or less, or the orifices may be equipped each with a valve member, a filter member or with a breakable membrane.

The proximal portion 111 of the reservoir 110 and the proximal end 151 of the housing 150 include a filling hole 155 that gives access to the inside of the reservoir 110 in order to fill up a drug composition. This filling hole 155 is intended to be sealed or closed by a cap (not represented) secured in a removable or in a non-removable manner to the housing 150 and/or to the reservoir 110. Alternatively, only the proximal portion 111 of the reservoir 110 may include a filling hole and the proximal end 151 of the housing 150 may serve as a cap.

Now considering FIG. 2, a general three-dimensional representation of the medical injection system 100 according to the present invention is shown. The reservoir 110 is not visible as it is hidden and embedded within the gas compartment 130 but two finger flanges 160 are visible on the distal end 142 of the piston 140. These finger flanges comprise a distal surface intended to be in contact with two front fingers of the medical caregiver, for example, the index finger and the middle finger. In addition, the proximal surface of the proximal end 151 of the housing 150 defines a handling surface 153 intended to receive a thumb of the same hand of the medical caregiver.

This way of grasping or prehension of the medical injection system 100 allows the medical caregiver to realize the pricking operation of the patient's skin with the thumb, which allows a precise control of the inserted needle depth. In addition, the distal portion 111 of the reservoir that surrounds a portion of the injection needle 120 may be used as a stop for the pricking operation and may be valuable for an accurate control of the inserted needle depth.

The injection operation can be performed by a squeezing movement of the front fingers toward the thumb, i.e. in the proximal direction, which is natural and conformable for a medical caregiver. In addition, this squeezing movement contributes to prevent any change in the inserted needle depth, thus simplifying the injection operation of a drug composition to a patient and preventing any variation of the inserted needle depth.

Figure 4:
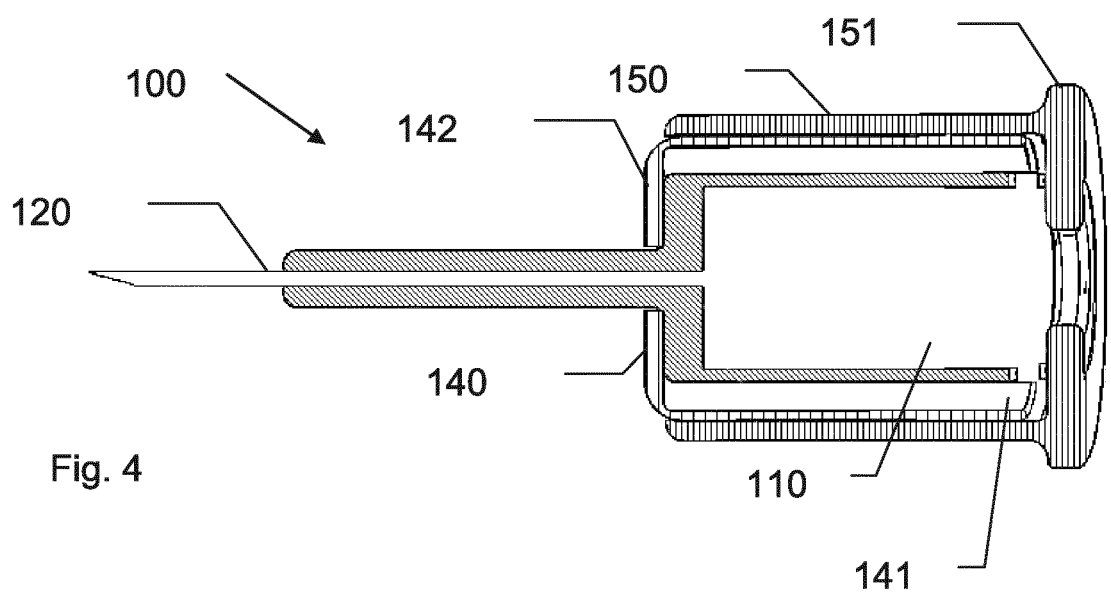
FIG. 4 is a cross-section view of the medical injection system according to FIG. 1 after an injection has been performed.

Now in operation, and with reference to FIGS. 3 and 4, a drug composition 170 is contained in the reservoir 110 and a medical caregiver grasps the medical injection system 100 as previously described. The medical caregiver first performs the pricking operation of the patient's skin i.e. inserts the injection needle 120 into the patient's body. The medical caregiver then performs the squeezing movement required for the injection operation. The injection operation is preferably performed when holding the medical injection system 100 vertically.

By squeezing the finger flanges 160 (not visible in FIGS. 3-4) toward the proximal end 151 of the housing 150, i.e. toward the thumb of the medical caregiver, the piston 140 is slid from the distal position shown in FIG. 3 to the proximal position shown in FIG. 4, i.e. toward the proximal end 151 of the housing 150. During this movement, the internal volume of the cavity defined by the gas compartment 130 is reduced and a pressure is applied on the gas contained in the gas compartment 130, as represented by the proximally-pointing horizontal arrows of FIG. 3. The gas is forced to flow into the reservoir 110 through the gas communication interface and the orifices 113, as represented by the transversally-pointing arrows of FIG. 3.

This transferred gas thus applies a pressure onto the drug composition 170, as represented by the distally-pointing horizontal arrow of FIG. 3, which forces the drug composition through the injection needle 120, and the drug composition enters the proximal end 121 of the injection needle 120 and is expelled through the distal end 122 into the patient's body.

At the end of the injection movement, i.e. in the proximal position of the movable potion 140 shown in FIG. 4, the distal end 142 of the piston 140 is nearby or in contact with the reservoir 110 and the proximal end 141 of the piston 140 is nearby or in contact with the proximal end 151 of the housing 150.

The gas compartment 130 allows decoupling the hand movement of the medical caregiver performing the injection from the injection of the drug composition as the force is transmitted by the compressed gas. In addition, the direction of the hand movement required to perform the injection operation is opposite to the injection direction, i.e. opposite to the distal direction. Because of this, only a limited attention is required for the injection movement and the piston 140 can merely be slid into the housing, from the distal position to the proximal position, and the transfer of the gas contained in the gas compartment 130 prevents, or at least reduces any jerking movement.

In addition, grasping of the medical injection system 100 is intuitive and allows easy control of the inserted needle depth by controlling the pressure applied on the proximal surface of the proximal end 151 of the housing 150, by the thumb of the medial caregiver. The hand position allowed by the present medical injection system 100 also allows to reduce any pain or tiredness in the hand of a medical caregiver, for example performing a number of injections a day.

Finally, the coaxial arrangement of the gas compartment 130 surrounding the reservoir 110 allows a compact design of the medical injection system 100, while avoiding any long and bulky packaging.

On an industrial point of view, the reservoir 110 may be attached to an injection needle 120 and a housing 150 and sterilized by a known method, such as steam or ethylene oxide. Such a sub-assembly can be shipped toward a filling line for example into a standard nest thanks to the radial rim of the proximal end 151. In the filling line, a drug is filled into the reservoir 110 by the filling hole 155 and the piston 140 is then attached to the housing 150. The filled and assembled medical injection system 100 may then be placed into a blister packaging before shipping to pharmacies and hospitals.

The medical injection system may further comprise a passive needle safety system (not represented), intended to secure the injection needle after the injection operation in order to prevent any undesired needle pricking. For example, the gas compartment may comprise a spring located between the housing and the piston or between the reservoir and the piston in order to bring the piston from the proximal position of FIG. 4 to a final, safety position wherein the piston is located around the distal end of the injection needle to hide and secure it. For example, the safety position may be obtained from locking means configured to lock the piston in a position distal to the distal position. These locking means may comprise snap features, such as a pin and a track.

Alternatively or in combination, the medical injection system may comprise a priming system (not represented), which requires a priming movement to allow an injection to be carried out. This priming movement may be for example the removal of a blocking element or the rotation of the piston in view of the housing. Alternatively, the reservoir and the piston may be fixed in rotation and the housing may comprise obturators blocking the orifices of the reservoir. A rotational movement of the piston in view of the housing may thus allow opening the orifices in order to perform the injection.

Although the present invention has been described and illustrated in detail, it is clearly understood that the same is by way of illustration and example only and is not to be taken by way of limitation, the scope of the present invention being limited only by the terms of the appended claims.

In particular, the reservoir may be fixed on an exterior surface of the housing of the gas compartment. In this embodiment (not represented), the reservoir and the piston may be parallel: their longitudinal axis may be parallel to the other. In addition, the piston may slide onto the housing.

Further, the gas compartment could be inserted into the reservoir, and the reservoir thus surrounds the gas compartment in this embodiment.

Then, the shape and relative dimensions of the different element of the medical injection system 100 may be adapted according to each particular volume and each particular use. The size, diameter and number of the finger flanges 160 can be chosen between all possible variants. The volume of the gas compartment 130 in the non-compressed state is not limited but is preferably similar to the volume of drug composition to be injected.

The invention claimed is:

1. A medical injection system adapted for a single-handed injection, the medical injection system comprising:
   a housing;
   a piston defining a cavity therein, wherein the piston is configured to move relative to the housing;
   a gas compartment configured to contain a gas, the gas compartment defined within the housing and the cavity of the piston; and
   a reservoir intended to contain a drug composition, the reservoir having a fluid exit configured to receive an injection needle,
   wherein the piston is configured to move proximally between a distal position defining a first volume of the gas compartment to a proximal position defining a second volume of the gas compartment smaller than the first volume, and
   wherein the gas compartment is configured to be in gas communication with the reservoir in order to force the drug composition through the fluid exit when the piston is moved proximally.

2. The medical injection system according to claim 1, wherein the reservoir is attached to the gas compartment.

3. The medical injection system according to claim 1, wherein a part of the piston is located distally to the reservoir at least in the distal position.

4. The medical injection system according to claim 1, wherein the reservoir is located within the gas compartment.

5. The medical injection system according to claim 1, wherein the gas compartment is located coaxially and around the reservoir.

6. The medical injection system according to claim 1, wherein a longitudinal symmetry axis of the reservoir is co-linear with a longitudinal symmetry axis of the gas compartment.

7. The medical injection system according to claim 1, wherein the reservoir comprises a proximal portion defining a handling surface which is adapted to accommodate a thumb of a user, and wherein the piston is provided with at least one finger flange adapted to accommodate at least another finger of the user.

8. The medical injection system according to claim 1, wherein a sealing member is provided between the piston and the gas compartment.

9. The medical injection system according to claim 1, wherein the gas compartment is configured to be in gas communication with a proximal portion of the reservoir.

10. The medical injection system according to claim 9, wherein a gas communication interface is provided between the piston and the reservoir, and wherein the gas communication interface comprises at least one orifice.

11. The medical injection system according to claim 10, wherein the gas communication interface is configured to prevent transmission of any liquid from the reservoir to the gas compartment.

12. The medical injection system according to claim 10, wherein the at least one orifice comprises a valve member, a filter member or a breakable membrane.

13. The medical injection system according to claim 10, wherein the at least one orifice is in a sidewall of the reservoir.

14. The medical injection system according to claim 1, wherein a proximal portion of the reservoir and a proximal end of the housing comprise a filling hole configured to introduce liquid directly into the reservoir.

15. The medical injection system according to claim 14, wherein a distal portion of the reservoir is provided with an injection needle.

16. The medical injection system according to claim 1, wherein the reservoir is directly attached to a proximal end of the housing.

17. The medical injection system according to claim 16, wherein the proximal end of the housing includes a filing hole leading into the reservoir.

* * * * *